United States Patent [19]
Herman

[11] Patent Number: 5,851,522
[45] Date of Patent: Dec. 22, 1998

[54] ENHANCING KERATINOCYTE MIGRATION

[75] Inventor: Ira M. Herman, Newton, Mass.

[73] Assignee: Trustees of Tufts College, Medford, Mass.

[21] Appl. No.: 484,382

[22] Filed: Jun. 7, 1995

[51] Int. Cl.$^6$ ................................................. A61K 38/46
[52] U.S. Cl. ................................ 424/94.67; 424/DIG. 13
[58] Field of Search .......................... 424/94.67, DIG. 13

[56] References Cited

U.S. PATENT DOCUMENTS

| | | | |
|---|---|---|---|
| 3,678,158 | 7/1972 | Sussman | 424/94.67 |
| 3,705,083 | 12/1972 | Chiulli | 924/94.67 |
| 4,174,389 | 11/1979 | Cope | 424/94.67 |
| 4,338,300 | 7/1982 | Gelbard | 424/94.67 |
| 4,524,065 | 6/1985 | Pinnell | 424/94.67 |
| 4,645,668 | 2/1987 | Pinnell | 424/94.67 |
| 5,173,295 | 12/1992 | Wehling | 424/94.67 |
| 5,279,825 | 1/1994 | Wehling | 424/94.67 |
| 5,393,792 | 2/1995 | Stern et al. | 514/777 |
| 5,514,370 | 5/1996 | Stern et al. | 424/78.06 |

OTHER PUBLICATIONS

Zimmerman, "The Importance of Cellagenase. for The Local Treatment of Major Burns", *In Collagenase*, pp. 131–141.

Herman, Journal of Cardiovascular Pharmacology 22 (Suppl. 4): 525–536 (1993), "Molecular Mechanisms Regulating The Vascular Endothelial Cell Motile Response to Injury."

Hubbel, JA et al., Chemical Engineering News, Mar. 13, 1995, pp. 42–53.

Nolte, C.J. et al., Journal of Anatomy 185 (Pt. 2), Oct., 1944, pp. 325–333.

Stoppie, P et al., European Journal of Morphology 31(1–2), 1993, pp. 26–29.

Hubbel, J A et al., Chemical Engineering News, Mar. 13, 1995, pp. 42–53.

Nolte, C.J et al., Journal of Anatomy 185 (Pt. 2). Oct., 1944, pp. 325–333.

Stoppie, P et al., European Journal of Morphology 31(1–2), 1993, pp. 26–29.

Hansbrough, J.F., et al., Journal of Burn Care & Rehabilitation 14(5): 1993, pp. 485–494.

*Primary Examiner*—John W. Rollins
*Attorney, Agent, or Firm*—Roland Plottel; John D. Upham

[57] ABSTRACT

This invention relates to the use of a particular form of collagenase substantially free of other proteinases to increase the motility of karatinocytes.

8 Claims, 2 Drawing Sheets

ENHANCING KERATINOCYTE MIGRATION

This invention generally relates to the use of a particular form of collagenase to increase the motility of keratinocytes.

BACKGROUND

Keratinocytes are the predominate cell type of the epidermis. They arise by mitotic division from the stem cells constituting the deepest layer of the epidermis. The keratinocytes migrate upwardly, changing in structure and function until they become mature keratinized cells at the surface of the skin and are eventually sloughed off.

The rate of healing of wounds is affected, inter alia, by the rate of keratinocyte migration and proliferation.

Collagenase has been used to ameliorate various pathologic conditions of the body, and the effect of endogenesis collagenase on certain body functions has been studied.

Chiulli and Wegman, U.S. Pat. No. 3,705,083 (1972), produced from *Clostridium histolyticum* a combination of collagenase and another protease, and used it in ointment to debride necrotic tissue from dermal lesions such as burns, infected wounds and ulcers. This ointment has been on the market for the past 25 years. They also proposed using the combination as an injectable solution to facilitate internal sloughing and reabsorption of physiologically antagonistic tissue.

Sussman, U.S. Pat. No. 3,678,158 (1972), injected purified collagenase into herniated intravertebral discs.

Cope, U.S. Pat. No. 4,174,389 (1979), used Clostridiopeptidase A collagenase for the selective lysis of collagen fibrils in the vitreous of the eye.

Pinnell, U.S. Pat. No. 4,524,065 (1985), treated mammalian cicatrices such as acne scars, keloids and other hypertrophic scars by intralesional injection of purified collagenase.

Wehling, U.S. Pat. No. 5,173,295 (1992) used purified collagenase to enhance regeneration of injured nerves.

Gelbard, U.S. Pat. No. 4,338,300 (1982), injected collagenase into the plaques of Peyronie's Disease.

W. E. Zimmerman, In Collagenase, ed. Mondl, I., (pp. 131–141) 1970 1st ed., Gordon and Breach, "The Importance of Collagenase for the Local Treatment of Major Burns," states that collagenase used on burns exerts a concomitant beneficial effect on the formation of tissue proliferations and may thus be used to advantage in the treatment of varying types of wounds.

Herman, *Journal of Cardiovascular Pharmacology* 22 (Suppl. 4): S25–S36 (1993), "Molecular Mechanisms Regulating the Vascular Endothelial Cell Motile Response to Injury," reported that a commercial non-homogeneous preparation of bacterial collagenase routinely used for the isolation of vascular cells from blood vessel segments increased the rate of migration of vascular endothelial cells on an injured epithelial cell-synthesized matrix in vitro from two to five times the rate for vascular endothelial cells on intact matrix.

THE INVENTION

The present invention enhances the migration and proliferation of keratinocytes in wound healing by contacting same with Clostridiopeptidase A collagenase (EC 3.4.24.3), obtained by fermentation of Clostridium histolyicum, that has been purified to be substantially free from other proteinases. Preferably, an open wound in the skin is treated by contacting exposed sub-cellular matrix with the said purified collagenase in an amount effective to enhance the rate of migration of keratinocytes towards the wound edges. Contacting keratinocytes means contacting them directly, and/or indirectly by contacting the sub-cellular matrix.

The purified collagenase is preferably applied as an aqueous solution, e.g. dissolved in phosphate-buffered saline. It may also be used in admixture with other pharmaceutically acceptable liquid or solid carriers including slow release carriers. The mature and use of such carrier is within the skill of the art.

Suitable concentrations may range from about 0.5 ABC units collagenase/ml or less up to about 150 ABC units/ml or more, i.e. about 5 $\mu$g/ml or less up to about 1,500 $\mu$g/ml or more. Concentrations often will be in the range of about 2 to about 50 ABC units/ml. The amount of the purified collagenase applied will be sufficient to increase substantially the migration rate of the keratinocytes towards the wound edges, preferably at least three-fold over the rate that would prevail without the treatment. Of course, the larger the wound the greater the amount of the purified collagenase to be used. Also, the more body fluid present or expected to be present in the wound, the higher the concentration of collagenase solution that will be used. The physician will use his/her professional judgment in these matters.

The potency assay of collagenase is based on the digestion of undenatured collagen (from bovine tendon) at pH 7.2 and 37° C. for 20–24 hours. The number of peptide bonds cleaved are measured by reaction with ninhydrin. Amino groups released by a trypsin digestion control are subtracted. One net ABC unit of collagenase will solubilize ninhydrin reactive material equivalent to 1.09 nanomoles of leucine per minute.

The assay of collagenases for other proteinases is based on ability to digest casein. This caseinase assay procedure combines (1) the idea of Reimerdes and Klostermeyer [methods Enzymol 45: 26–28 (1976)] to determine the amount of primary amino groups present int he trichloroacetic acid-soluble digestion products with (2) the method of Udenfriend et al. [Science 178: 871–2 (1972)] to detect the primary amino groups fluorometrically. The sample is incubated with added casein, which is not soluble, at 37° C. for 20–22 hours. The sample is quenched with trichloroacetic acid and the undigested casein is then centrifuged out. Solubilized peptides result from the action of caseinase in the sample on the added casein. Each peptide molecule has a terminal primary amine group. Fluorescamine™ is added to the supernatant and reacts with primary amine groups producing fluorescent molecules. The fluorescence is measured and a calculation gives a caseinase activity as FFC units.

The present invention in another aspect provides a method of enhancing the migration and proliferation of keratinocytes in the growth of artificial skin in vitro by growing the artificial skin in the presence of added Clostridiopeptidase A collagenase that has been purified to be substantially free from other proteinases. Artificial skins are useful as temporary skin grafts for burns and ulcers, and are used for testing of cosmetics and household cleansers in vitro.

In applying the present invention, the purified Clostridiopeptidase A collagenase described herein is added to provide a concentration in the growth medium of from about 0.5 ABC units collagenase/mil or less to about 150 ABC units/ml or more, thereby enhancing the migration and proliferation of keratinocytes. some examples of artificial skins whose growths can be favorably affected by this invention follow.

Advanced Tissue Sciences of La Jolla, Calif. has marketed Dermagraft™ as a skin substitute. A mesh scaffold made from lactic acid-glycolic acid copolymer, about 90μ thick with openings of about 200–220 μm was seeded with skin fibroblasts from neonatal foreskins. The cells bridge sufficiently to secrete skin proteins and proteoglycans. See Hubbell, JA et al. Chemical and Engineering News pp. 42–53 (Mar. 13, 1995).

Graftskin™ has been introduced by Organogenesis of Canton, Mass. See Nolte CJ et al. Journal of Anatomy 185 (Pt. 2): 325–33 (1944 Oct.) Advanced Tissue Sciences has also marketed Skin$^2$™ as a skin substitute for in vitro testing of cosmetics, household chemicals and other products. See Stoppie P et al. European Journal of Morphology 31 (1–2): 26–9 (1993).

See also Hansbrough JF et al., Journal of Burn Care & Rehabilitation 14(5): 485–94 (1993).

EXPERIMENTAL

The effect of collagenases of varying purities on the motility and proliferation of keratinocytes was determined in vitro, employing sub-cellular matrices synthesized from vascular endothelial cells.

Vascular endothelial cell culture

Endothelial cells are isolated from living bovine vessel segments. Rings of aortae are obtained on ice from an abattoir sutured at the ends and filled with balanced salts (BSS). Endothelial cells are released from the intima using 0.1% collagenase dissolved in BSS by incubation at 37° C. for 30 minutes-one hour. Cells are pelleted at 200g for 5 minutes at room temperature and the resultant pellet resuspended in growth media containing 5% calf serum. Cells are plated into tissue culture at 50K cells/25 cm$^2$. Following growth to confluence, cells are typsinized and passaged at 1:5 split. Cells are used between passages 5–15.

Endothelial-derived matrix:

One week post-confluent endothelial cells are washed with BSS prior to lysis in sterile solution containing 0.5% sodium deoxycholate in 0.015M NaCl, 0.001M EGTA buffered with 0.02M Tris-Cl, pH 7.8 with 0.001M phenyl methyl sulfonyl fluoride (PMSF) as a protease inhibitor. Two room temperature detergent treatments, each lasting 15 minutes, are followed by five washes with BSS, each wash lasting 5 minutes. Keratinocytes are then plated directly onto washed matrices or matrices are digested with collagenase solutions.

Treating matrices with collagenases:

Endothelial matrices, prepared as described above are treated for 60 minutes at 37° C. with various preparations of collagenases dissolved in BSS (0.9% sodium chloride) containing 2mM CaCl$_2$. Collagenase dose ranges from 0–128 U/ml; 1 U/ml =10 μg/ml collagenase. Matrices treated with the enzyme are then washed with BSS without calcium and keratinocytes and then plated. (U means ABC units).

Human keratinocytes:

At circumcision, foreskins are placed into GIBCO Keratinocyte-SFM containing Gentamycin (Cat.nos. 17005–018 and 157–015) at 5 μg/ml. Tissue is then rinsed in BSS with gentamycin prior to cutting into pieces of 3–4 mm$^2$. Tissue pieces are then incubated for 18 hrs at 4° C. in 25U/ml dispase (Collaborative Research cat.no. 40235). After dispase incubation, the epidermal layer of human keratinocytes is lifted from the dermis and placed into 15 ml centrifuge tubes containing trypsin-EDTA (2ml). Following a 15 minute incubation at 37° C., cells are sedimented and plated in Keratinocyte-SFM at an initial seeding density of 3×10$^6$ cells/T (75 cm$^2$) flask. cells are incubated and passaged using trypsin-EDTA when the flask is 60–70% confluent.

Motility and growth studies:

For cell motility (wound healing) studies, keratinocytes are plated at near-confluent densities on intact or collagenase-treated matrices (100 K cells/cm$^2$). Cells plated on glass microscope cover slides with matrices attached are then placed into a specially-designed culture chamber that mounts on the stage of an inverted, interference or phase contrast light microscope. Cells are warmed to 37° C. while viewed using video-enhanced optics coupled with computer-assisted imaging work station and software developed in the lab to automatically track living cell migration (Cell Tracker, Askey and Herman, 1988; Computers and Biomedical Res. 21:551–61). Keratinocytes bordering artificially created wounds made with fire-polished pasteur pipets, or keratinocytes at the edge of intact sheets, are then recorded for motility as a function of matrix condition.

For cell proliferation studies, keratinocytes are plated in triplicate onto plastic or matrix (intact or collagenase treated; doses from 0–64 U/ml, with 4 U/ml sufficient to deliver maximal proliferative responses seen within 7 days post-plating) at 2–5K cells/cm$^2$. Cells are fed on alternate days with Keratinocyte-SFM and triplicate wells of cells counted directly using a Coulter Counter, ZF. Cell counts, together with errors of the mean are plotted as a function of time and condition using Kaleidograph, a software support compatible with the MacIntosh computer workstation in the lab.

Crude Collagenase:

This was obtained substantially as described by Chiulli and Wegman in U.S. Pat. No. 3,705,083 (see page 1 above), with minor modifications. It is the powder used as the active ingredient in Santyl® Ointment. The collagenase content ranges from 100–300 ABC units per mg, and the proteanase content ranges from 30 to 240 FFC units/mg.

Cleaned-Up Collagenase:

Crude Collagenase was suspended in distilled water and after thorough stirring was centrifuged. The centrifuge tubing were decanted and the supernatant was again centrifuged. The resultant clarified solution was "cleaned up" product.

ABC Purified Collagenase:

This was prepared from crude collagenase by chromatography substantially eliminating other proteinases. The purified collagenase used contained only about 0.1 FFC units proteinases per mg.

Pool 3A

This was a combination of fractions discarded in the chromatography yielding Purified Collagenase.

Clostripain

A proteinase present in crude. This sample was a commercially available clostripain.

The collagenases were provided by Advance Biofactures Corporation of Lynbrook, N.Y. 11563.

In the following tests, the concentration of collagenase used in all of the samples of varying purities was 4 ABC units per ml.

BRIEF DESCRIPTION OF THE DRAWINGS

FIG. I presents graphically the motility (migration) data.

FIG. II presents graphically the proliferation data.

Figure 1:
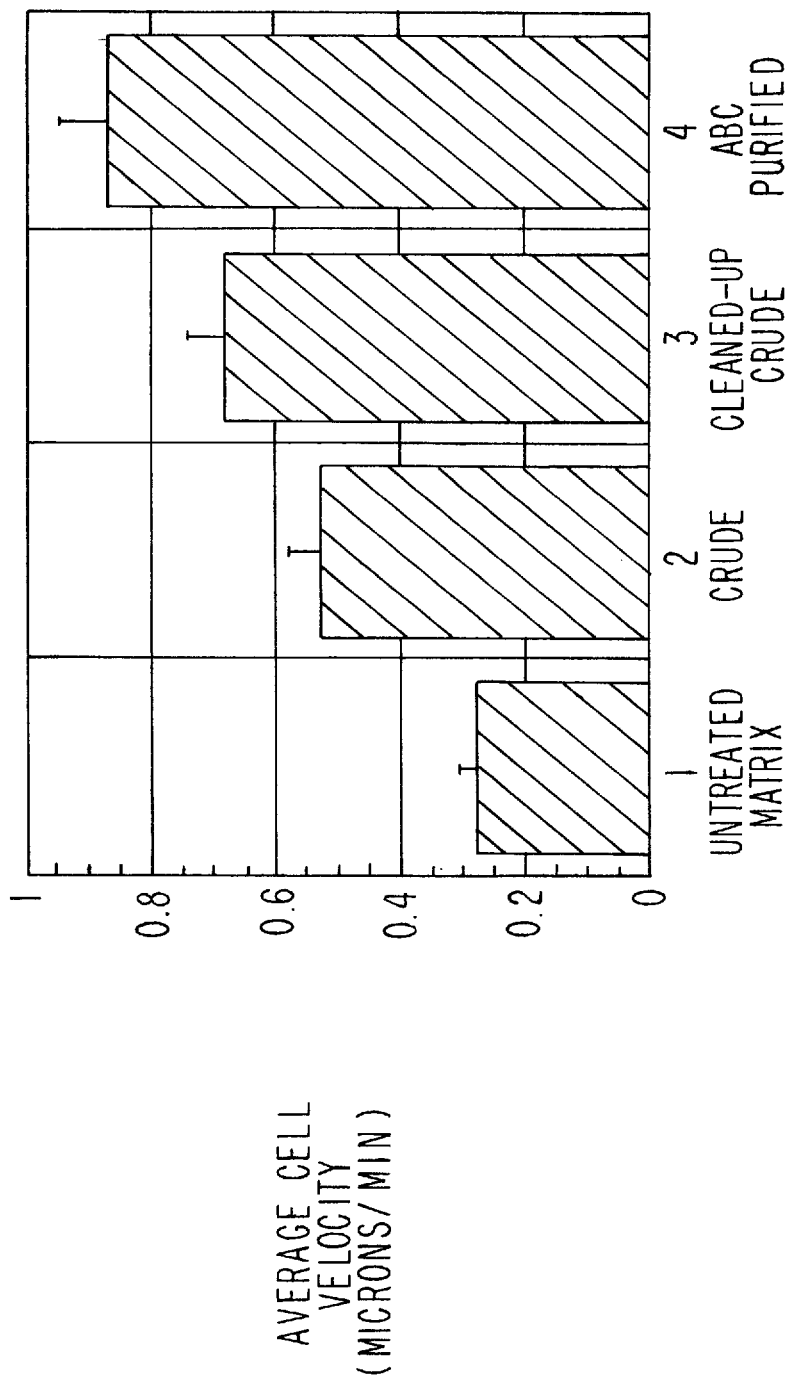
Figure 2:
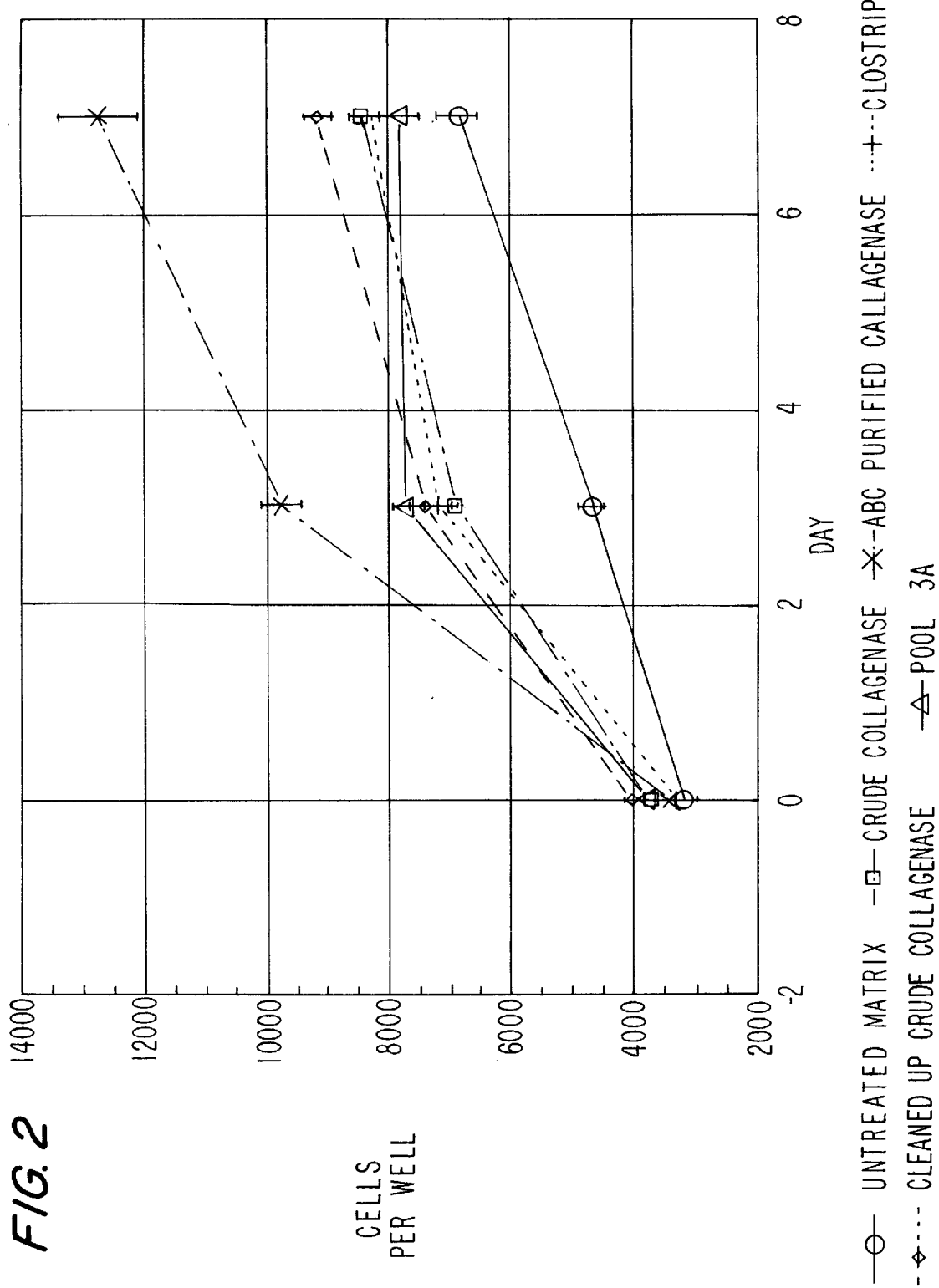

Table I gives the migration results in terms of Migration Index.

Table II gives the proliferation results in terms of Proliferation Index.

TABLE I

MATRIX MODULATES KERATINOCYTE SHEET MIGRATION

| Matrix | Migration Index (MI) $ |
| --- | --- |
| Untreated | 1.0 |
| ABC Purified | 3.1 |
| Cleaned-Up Crude Collagenase | 2.4 |
| Crude collagenase | 1.9 |

$MI = mean motility (experiment)/mean motility (control)

TABLE II

MATRIX MODULATION OF KERATINOCYTE PROLIFERATION

| Matrix | Proliferation Index (PI) $ |
| --- | --- |
| Untreated | 1.0 |
| ABC Purified | 2.1 |
| Cleaned-Up Crude Collagenase | 1.4 |
| Crude Collagenase | 1.3 |
| Clostripain | 1.3 |
| Pool 3A | 1.3 |

$PI = mean cell counts (experiments)/mean cell counts (control)

In these tests, treatment of the extracellular matrix with the purified collagenase potentiated keratinocyte migration 3-fold over the untreated matrix control, and potentiated keratinocyte proliferation 2-fold over the untreated matrix control. Other similar tests gave migration rates up to 10-fold over untreated matrix. Further in every instance the results with the purified collagenase were superior to those obtained with the less pure (cleaned up crude and crude) collagenases.

Another series of tests employed three kinds of synthetic sub-cellular matrices, prepared respectively from normal skin fibroblasts, endothelial cells, and cells from keloid scars. Each was treated with concentrations of purified collagenase ranging from 1 ABC unit/ml to 64 ABC units/ml, and the rate of cell growth (proliferation) is measured. With each matrix the growth rate at 64 units/ml was taken as the rate beyond which a higher dosage would have only limited effect. The dosage giving 50% of that growth rate (designated ED 50) was for each matrix about 1 ABC unit/ml.

I claim:

1. A method of enhancing the migration and proliferation of keratinocytes in human wound healing which comprises contacting same with an effective amount of purified Clostridiopeptidase A collagenase substantially free from other proteinases.

2. A method according to claim 1 wherein said collagenase is applied in the form of an aqueous solution containing from about 0.5 ABC units collagenase/ml to about 150 ABC units/ml.

3. A method according to claim 2 wherein the collagenase concentration is within the range of about 2 to about 50 ABC units/ml.

4. A method of treating an open wound in human skin which comprises contacting exposed sub-cellular matrix with purified Clostridiopeptidase A collagenase substantially free from other proteinases in a concentration effective to enhance the rate of migration of keratinocytes towards the wound edges.

5. A method according to claim 4 wherein said collagenase is applied in the form of an aqueous solution containing from about 0.5 ABC units collagenase/ml to about 150 ABC units/ml.

6. A method according to claim 5, wherein the collagenase concentration is within the range of about 2 to about 50 ABC units/ml.

7. A method of enhancing the migration and proliferation of keratinocytes in mammalian wound healing which comprises contacting same with an effective amount of purified Clostridiopeptidase A collagenase substantially free from other proteinases.

8. A method of treating an open wound in mammalian skin which comprises contacting exposed sub-cellular matrix with purified Clostridiopeptidase A collagenase substantially free from other proteinases in a concentration effective to enhance the rate of migration of keratinocytes at the wound edges.

* * * * *